United States Patent
Desinger et al.

(10) Patent No.: US 7,828,799 B2
(45) Date of Patent: Nov. 9, 2010

(54) PROBE ARRANGEMENT

(75) Inventors: Kai Desinger, Berlin (DE); Markus Fay, Berlin (DE); Thomas Stein, Berlin (DE); Rainer Rothe, Berlin (DE)

(73) Assignee: Celon AG, Teltow, Berlin (DE)

( * ) Notice: Subject to any disclaimer, the term of this patent is extended or adjusted under 35 U.S.C. 154(b) by 0 days.

(21) Appl. No.: 10/729,040

(22) Filed: Dec. 5, 2003

(65) Prior Publication Data
US 2004/0167517 A1 Aug. 26, 2004

Related U.S. Application Data

(63) Continuation of application No. PCT/EP02/05778, filed on Jun. 7, 2001.

(51) Int. Cl.
*A61B 18/18* (2006.01)

(52) U.S. Cl. .............. 606/50; 606/41; 606/48

(58) Field of Classification Search ............. 606/27–52, 606/16, 20–25; 607/69–101, 104; 219/229, 219/234, 239
See application file for complete search history.

(56) References Cited

U.S. PATENT DOCUMENTS

| | | | | |
|---|---|---|---|---|
| 4,557,272 A | * | 12/1985 | Carr | 600/549 |
| 4,832,048 A | | 5/1989 | Cohen | |
| 5,451,224 A | * | 9/1995 | Goble et al. | 606/48 |
| 5,458,597 A | * | 10/1995 | Edwards et al. | 606/41 |
| 5,961,471 A | * | 10/1999 | Nickson | 600/546 |
| 6,106,524 A | * | 8/2000 | Eggers et al. | 606/50 |
| 6,134,476 A | * | 10/2000 | Arndt et al. | 607/101 |
| 6,149,648 A | | 11/2000 | Cosmescu | |
| 6,197,024 B1 | | 3/2001 | Sullivan | |
| 6,210,411 B1 | | 4/2001 | Hofmann | |
| 6,245,062 B1 | * | 6/2001 | Berube et al. | 606/33 |
| 6,673,068 B1 | * | 1/2004 | Berube | 606/33 |
| 6,878,147 B2 | * | 4/2005 | Prakash et al. | 606/33 |
| 6,976,986 B2 | * | 12/2005 | Berube | 606/33 |
| 7,387,628 B1 | * | 6/2008 | Behl et al. | 606/41 |

FOREIGN PATENT DOCUMENTS

EP 0 866 672 11/1996

(Continued)

OTHER PUBLICATIONS

International Search Report for PCT (5 pages).

*Primary Examiner*—Ahmed M Farah
(74) *Attorney, Agent, or Firm*—Beck & Tysver, P.L.L.C.

(57) ABSTRACT

The disclosure provides a probe arrangement having a distal probe tip and a proximal hand portion for the electrothermal coagulation of tissue. The probe arrangement has at least a first and a second electrode in the region of the distal probe tip. An inner conductor of the probe arrangement extends from the distal probe tip to the proximal hand portion and contacts the first electrode in the distal probe tip. An outer conductor of the probe arrangement extends from the distal probe tip to the proximal hand portion and serves to electrically contact the second electrode in the distal probe tip. The inner and outer conductors of the probe arrangement are electrically insulated from each other. Furthermore the inner conductor is selected in such a way that the flexural stiffness of the probe arrangement is increased between the probe tip and the hand portion.

16 Claims, 14 Drawing Sheets

FOREIGN PATENT DOCUMENTS

| | | |
|---|---|---|
| EP | 1 025 807 | 8/2000 |
| JP | 6312028 | 11/1994 |
| WO | WO 81 03272 | 11/1981 |
| WO | WO 95 10320 | 4/1995 |
| WO | WO 96 18349 | 6/1996 |
| WO | WO 96 34569 | 11/1996 |
| WO | WO9700647 | 1/1997 |
| WO | WO 9717009 | 5/1997 |
| WO | WO 98 19613 | 5/1998 |
| WO | WO 99 11186 | 3/1999 |
| WO | WO 00 09208 | 2/2000 |
| WO | WO 00 36985 | 6/2000 |

* cited by examiner

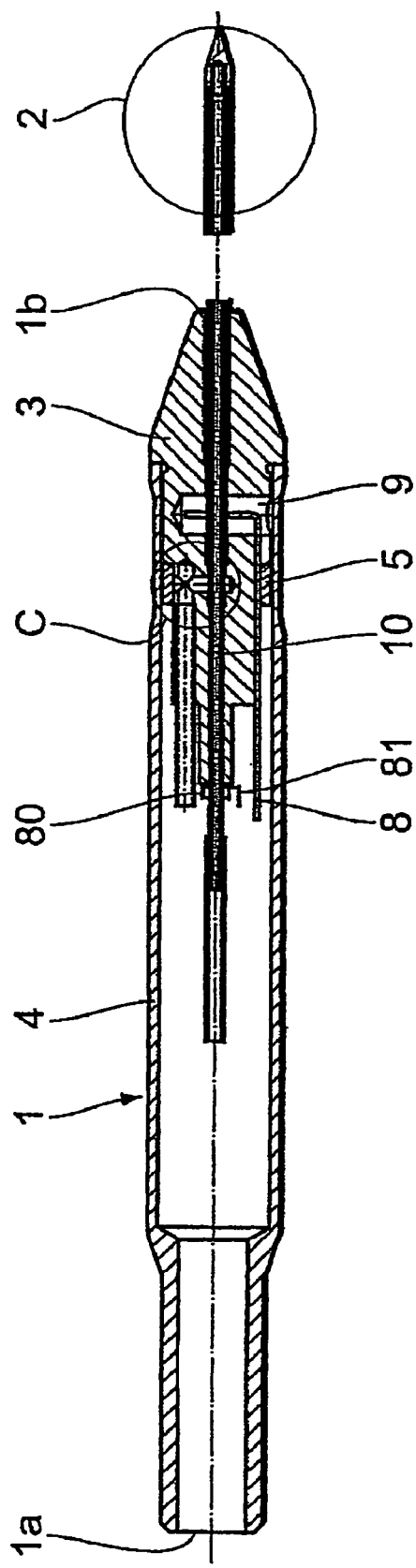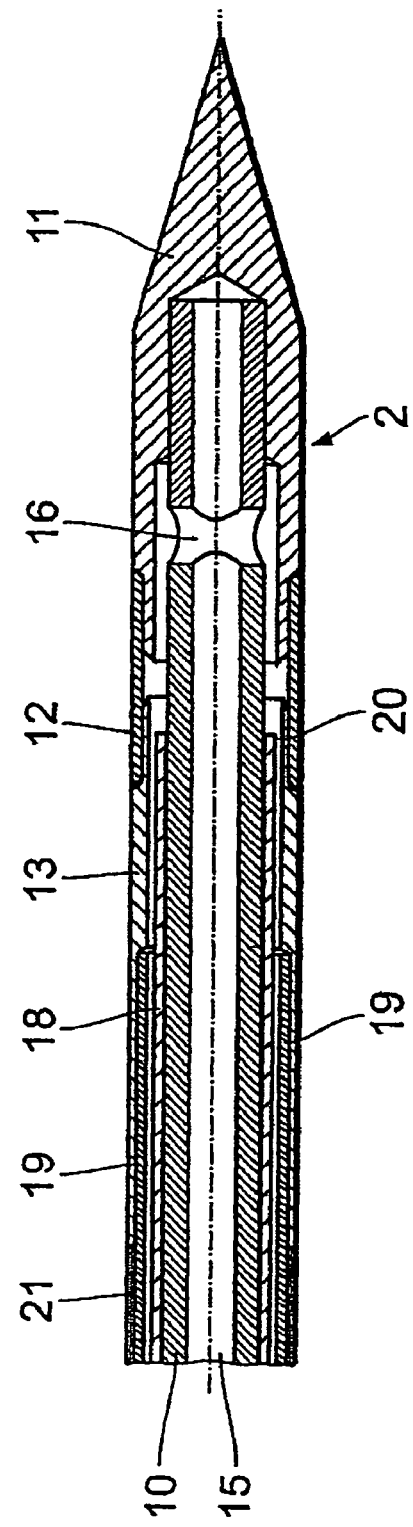
Fig. 1a
Fig. 1b

PROBE ARRANGEMENT

This application is a continuation of PCT/EP02/05778 filed Jun. 7, 2001.

BACKGROUND OF THE INVENTION

The present disclosure concerns a probe arrangement comprising a distal probe tip and a proximal hand portion for the electrothermal coagulation of tissue. The probe arrangement includes at least a first and a second electrode in the region of the distal probe tip, an inner conductor that extends from the distal probe tip to the proximal hand portion and is adapted to electrically contact the first electrode in the distal probe tip, and an outer conductor which extends from the distal probe tip to the proximal hand portion and is adapted to electrically contact the second electrode in the distal probe tip, wherein the inner and outer conductors are electrically insulated from each other.

Using high-frequency (HF) alternating currents (for example in the frequency range of between 300 KHz and 2 MHz) for the production of high temperatures for tissue coagulation and for tissue separation has long been known in surgery. In arrangements of that kind for bipolar HF-thermotherapy, both electrodes are connected to an HF-generator and are arranged in dimensions that are fixed with each other, for example on an insulating carrier. They are placed by the operator in the immediate proximity of the treatment location and in general are also actively guided.

WO 97/17009 discloses a bipolar electrode arrangement with a liquid duct, by way of which flushing liquid can be introduced into the region of operative intervention. Two or three electrodes are arranged in the form of cone portions on a conical distal tip of the instrument, which can be introduced into the tissue. The electromagnetic HF-field is formed between the electrodes and is intended to coagulate the surrounding tissue.

WO 96/34569 and the documents referred to in the associated International Search Report disclose systems and methods of coagulating body tissue while observing a pre-calculated maximum tissue temperature. Liquid cooling or thermoelectric cooling is provided during the actual tissue coagulation process. These known arrangements are intended for insertion into body cavities by way of natural accesses.

U.S. Pat. No. 4,832,048 and WO 95/10320, WO 99/11186 or EP 96 945 879.3 and WO 98/19613, WO 96/18349 and WO 81/03272 further disclose surgical instruments that, by means of a bipolar electrode arrangement, treat tissue by means of HF-thermotherapy.

WO 00/36985 discloses an electrode arrangement for a surgical instrument for the electrothermal coagulation of tissue. Such an electrode arrangement is shown in FIG. 13. The arrangement has an electrically conductive front cylinder 110 at the distal end of the instrument with a distal tip 112 and a cylindrical first electrode 182, a tubular outer conductor proximally adjoining the front cylinder, with a cylindrical second electrode 184, and an insulator element 170a between the front cylinder 110 and the outer conductor. The electrodes are connectable to an alternating current voltage source.

In that arrangement the first electrode 182 is in the form of a self-supporting tube portion that is disposed between the front cylinder 110 and an insulating tubular first carrier 170a. The second electrode 184 is also in the form of a self-supporting tube portion that is arranged between the first carrier 170a and a second tubular carrier 170b. The end portions of the electrodes 182, 184 rest on the front cylinder 110 and the first and second carriers 170a, b by way of a predetermined longitudinal portion. In addition, within the hollow duct 176 there is a flushing hose 10 that passes from the proximal end of the instrument to the front cylinder and is to say also through the tube portions forming the electrodes. This extends towards the front cylinder 110 and delivers liquid at the distal end into the hollow duct 176 in which the liquid flows back to the proximal end of the instrument. The electrodes 182, 184 are electrically contacted by way of wires 190.

It is also possible to use a cooling fluid for cooling an electrode arrangement. In this connection, that cooling fluid can be gaseous or liquid.

The known surgical instruments for bipolar HF-thermotherapy often suffer from a lack of strength.

SUMMARY OF THE INVENTION

An object of the disclosure is to provide a probe arrangement for electrothermal coagulation of tissue having improved strength. This is attained by a probe arrangement of the kind set forth above with additional features described below.

In this respect the disclosure is based on the idea of providing a probe arrangement having a distal probe tip and a proximal hand portion for the electrothermal coagulation of tissue. The probe arrangement has at least a first and a second electrode in the region of the distal probe tip. An inner conductor of the probe arrangement extends from the distal probe tip to the proximal hand portion and electrically contacts the first electrode in the distal probe tip. An outer conductor of the probe arrangement extends from the distal probe tip to the proximal hand portion and serves to electrically contact the second electrode in the distal probe tip. The inner and outer conductors of the probe arrangement are electrically insulated from each other. The inner conductor is further selected in such a way that the flexural stiffness of the probe arrangement between the probe tip and the hand portion is increased.

The advantages that the disclosure entails are that the strength and stiffness required for the probe arrangement are thus provided.

A positively locking or force-locking connection of the outer conductor and also the inner conductor to the probe tip on the one hand and the hand portion on the other hand provides that both the outer conductor and also the inner conductor advantageously contribute to the geometrical moment of inertia and thus enhance the flexural strength.

In an embodiment of the disclosure the inner conductor is connected to the hand portion and the probe tip in such a way that the inner conductor is under tensile stress and the outer conductor is under compression stress. That leads to a further increase in the stability of the probe arrangement.

In a embodiment of the disclosure the inner conductor is in the form of a metal tube. Using a metal tube gives the advantage that the metal tube serves as an electrical feed line for the first electrode, for the supply of the cooling medium, and for increasing the stiffness and breaking strength of the probe arrangement.

In a further embodiment of the disclosure the distal end of the inner conductor can be screwed to the probe tip while the proximal end of the inner conductor is braced in relation to the hand portion. This permits rapid fitting and easy replacement of the individual parts of the probe arrangement without in that respect adversely affecting the stability of the probe arrangement.

In a further embodiment of the disclosure there is provided an insulator between the inner and outer conductors in order to electrically insulate the inner conductor from the outer conductor. This makes it possible to avoid unwanted short-circuits between the inner and outer conductors, which can sensitively disturb operation of the probe arrangement.

In yet a further embodiment of the disclosure the inner and outer conductors and the insulator are arranged in mutually coaxial relationship.

In a particularly preferred embodiment of the disclosure the inner conductor has a hollow duct that feeds cooling or heating fluid from the proximal end into the distal end. At its distal end the inner conductor has a through bore from which the fluid supplied through the hollow duct can flow away. Provided between the insulator and the outer conductor is an intermediate space in which the fluid flowing out of the through bore of the inner conductor is taken back to the proximal end. Such an arrangement provides cooling or heating of the probe arrangement so that the probe arrangement is maintained at a defined temperature so that defined coagulation conditions obtain.

In a further embodiment of the disclosure the first electrode is in the form of a tip electrode and the second electrode is in the form of a shaft electrode.

In a further preferred embodiment of the disclosure provided between the shaft electrode and the tip electrode is an insulator element that is preferably of an annular configuration and is adapted to insulate the tip electrode from the shaft electrode for avoiding short-circuits.

In a further preferred embodiment of the disclosure the probe arrangement has an insulating tube that is fitted around the outer conductor to insulate it electrically from adjoining tissue. This avoids unwanted coagulation of the tissue in the region of the outer conductor, but coagulation occurs only in the region between the shaft electrode and the tip electrode.

In a further embodiment of the disclosure the hand portion has a first hand portion element that receives the proximal ends of the inner conductor, the outer conductor, the insulator and the insulation tube.

In a further preferred embodiment of the disclosure the first hand portion element has a first blind bore and a longitudinal slot that serve to guide an electrically conductive spring wire in the longitudinal slot from the proximal end of the first hand portion element to the first blind bore in order to electrically contact the outer conductor in the first blind bore.

In a further particularly preferred embodiment of the disclosure the first hand portion element also has a transverse bore and a second blind bore. The second blind bore is further connected to the intermediate space between the insulator and the outer conductor. The transverse bore and the second blind bore cross each other and thus there is a communication between the proximal end of the hand portion element and the intermediate space. Therefore, the fluid flowing back from the distal end in the intermediate space can escape by way of the second blind bore and the transverse bore through the first hand portion element.

In still a further preferred embodiment of the disclosure the inner conductor at its proximal end has a male screwthread which is designed to brace the inner conductor with a threaded nut against the first hand portion element. That provides for particularly easy assembly of the probe arrangement.

In a further embodiment of the disclosure the cooling fluid is barely electrically conducting or non-conducting altogether. Preferably, the cooling fluid represents deionized water. Such a cooling fluid can be used for the insulation between the inner and outer conductors.

BRIEF DESCRIPTION OF THE FIGURES

Embodiments by way of example of the invention are described in greater detail hereinafter with reference to the drawing in which.

DETAILED DESCRIPTION OF THE FIGURES

Figure 1C:
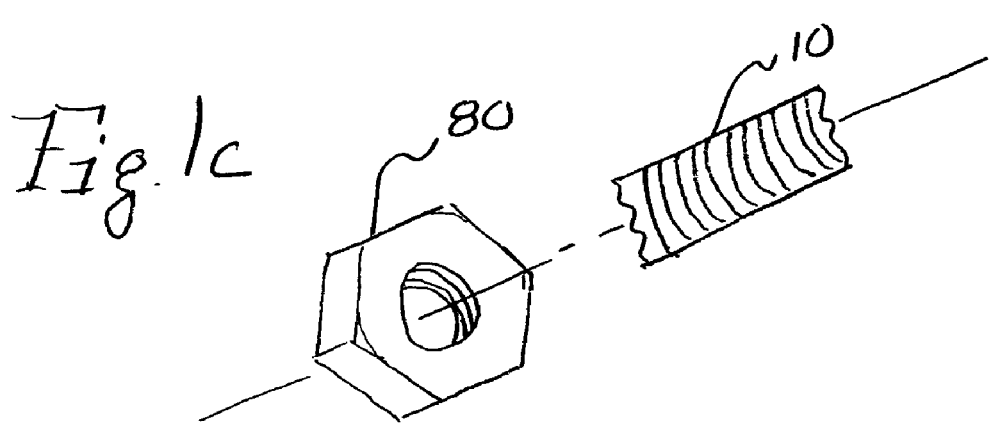
FIG. 1 is a view in section of the probe arrangement with a hand portion (FIG. 1a) and a distal probe tip (FIG. 1b) and a partial, exploded, enlarged view of an inner conductor and a mating nut (FIG. 1c)

FIGS. 1a and b show a view in section through a probe arrangement comprising a hand portion (FIG. 1a) and a probe tip (FIG. 1b). The probe arrangement has a hand portion 1 at the proximal end and a probe tip 2 at the distal end, that are connected substantially by a hollow-cylindrical inner conductor 10 and a hollow-cylindrical outer conductor 19 in spaced relationship with the inner conductor 10.

At the distal end of the probe the probe tip 11 is connected to the inner conductor 10 by way of a screw connection 17. In this arrangement the probe tip 11 is in the form of a tip electrode 11 that is electrically contacted by the inner conductor 10. Adjoining the proximal end of the tip electrode 11 is an insulator ring 12 and a shaft electrode 13. In turn, adjoining the shaft electrode 13 is an outer conductor 19 so that the shaft electrode 13 is electrically connected to the outer conductor 19. A hollow-cylindrical insulator 18 is disposed between the shaft electrode 13 and the outer conductor 19 and the inner conductor 10. The outer conductor 19, the insulator 18 and the inner conductor 10 thus form a coaxial arrangement.

Between the insulator layer 18 and the outer conductor 19 there is a hollow space 20 that extends from the distal end to the hand portion 1. Disposed around the outer conductor 19 is an insulation tube 21 that adjoins the proximal end of the shaft electrode 13. The inner conductor 10 has a through bore 16 at its distal end.

The outside diameters of the tip electrode 11, the insulator ring 12, the shaft electrode 13 and the insulation 21 of the outer conductor 19 correspond to each other.

As shown in FIG. 1a the hand portion 1 is composed of two elements 3, 4. The first hand portion element 3 is of a substantially conical configuration at its distal end 3b while is proximal end 3a is substantially cylindrical. The hand portion element 4 is substantially cylindrical and is of a hollow-cylindrical configuration at its distal end 4b. A clamping ring 5 and a proximal end 3a of the hand portion element 3 are introduced into the distal end 4b of the hand portion element 4, in order to substantially form the hand portion 1. The probe line joins the conical distal end 3b of the hand portion element 3 and the probe tip 2 is disposed at the distal end thereof.

Provided on the longitudinal axis of the hand portion element 3 is a through bore, through which the hollow inner conductor 10 completely and the outer conductor 19 spaced in relation to thereto, at least in a portion-wise manner, are passed to the probe tip 11. The hand portion element 3 has a first blind bore 9, a transverse bore 6—which is adjoined by a further transverse bore 30—and a second blind bore 31, the transverse bore 30 and the blind bore 31 intersecting at a right angle. A spring wire 8 which is bent at a right angle at its one end is used for electrical contacting of the outer conductor 19 in the blind bore 9.

The inner conductor 10 has a screwthread at its proximal end so that—in the inserted condition—the inner conductor 10 can be screwed by way of a nut 80 in relation to the hand portion element 3. A contact tongue 81 which is used for contacting of the inner conductor 10 can be provided between the nut 80 and the hand portion element 3.

Fluid can be conveyed through the hollow duct 15 of the inner conductor 10 from the proximal end—the hand portion 1—into the distal end, that is the probe tip 2, for cooling the probe tip 2, during an operation for the coagulation of tissue. The fluid arriving from the hand portion 1 in the hollow duct 15 flows out through the through bore 16 at the distal end of the inner conductor 10 and then flows back from the distal end to the proximal end through the intermediate space 20 between the inner conductor 10 and the shaft electrode 13 as well as the outer conductor 19. The intermediate space 20 is connected in the hand portion element 3 to the blind bore 31 so that the fluid flowing back from the distal end can escape by way of the blind bore 31 and the transverse bores 30 and 6 connected thereto. The fluid flowing into that hollow duct 15 and the fluid flowing out of the transverse bore 6 can be connected to an external cooling circuit.

Preferably the feed and discharge flow of the cooling fluid have different connections, such as for example male or female, in order to prevent confusion.

The cooling of the electrode surfaces by means of a flushing liquid provides that the so-called "hot spot" of coagulation is displaced by between two and three millimeters from the surface of the instrument into the tissue. Cooling ensures that the tissue-electrode contact face is always kept below a predetermined temperature and therefore does not dry out to such a great degree that the input of energy into the adjoining tissue is also ensured over a relatively long period of time.

Figure 2:
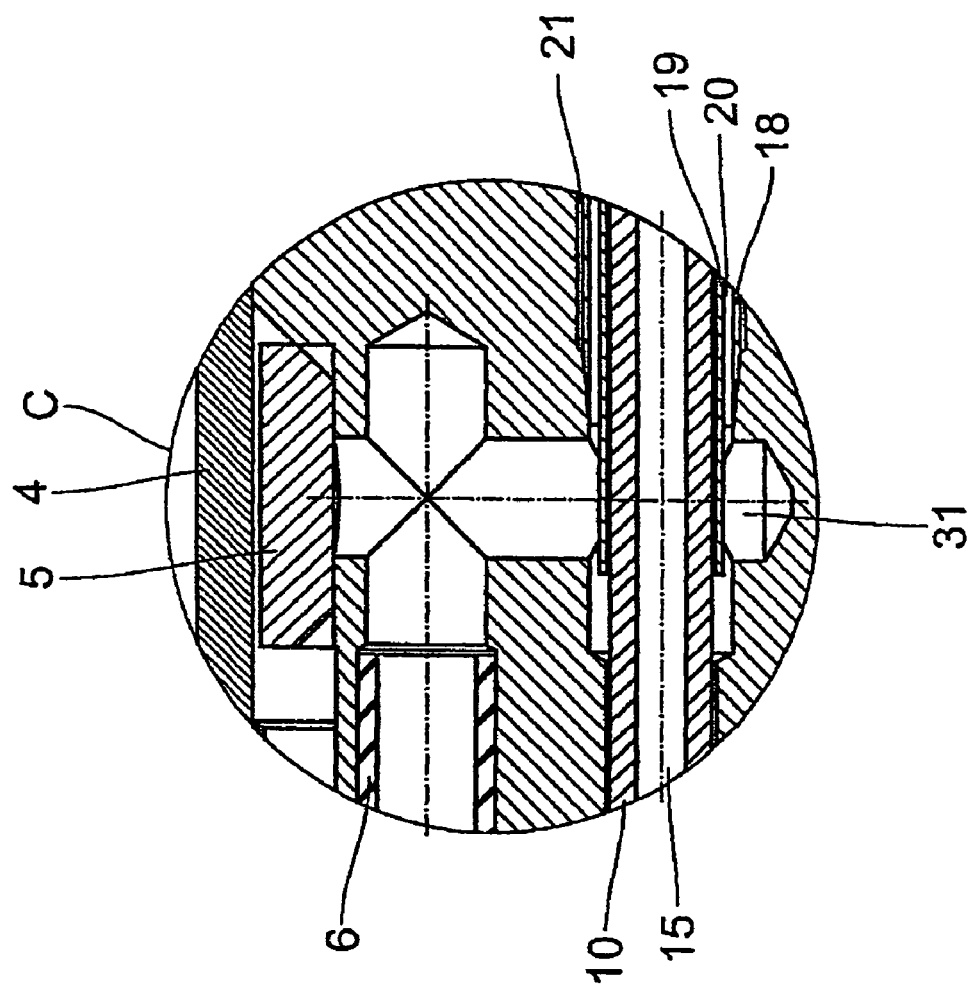
FIG. 2 shows a sectional view of the portion C in FIG. 1a, FIG. 3 shows a rear view and a sectional view of a probe tip 11 from FIG. 1b.

FIG. 2 shows a view on an enlarged scale of the portion C from FIG. 1a. The intermediate space 20 between the insulator 18 and the outer conductor 19 is connected to the blind bore 31. The inner conductor 10 is shown in the inserted condition, in FIG. 2. The insulator 18 extends from the distal end of the probe line to behind the blind bore 31 while the outer conductor 19 extends to shortly before the blind bore 31. In contrast the insulation layer 21 of the outer conductor 19 only extends to the level of the clamping ring 5. The blind bore 31 is crossed by the transverse bore 30. A further transverse bore 6 adjoins the transverse bore 30.

As the blind bore 31 and the transverse bore 30 are in communication with each other and the transverse bore 6 also goes into the transverse bore 30, there is a communication between the transverse bore 6 and the intermediate space 20. Fluid flowing back from the distal end of the probe can thus escape by way of the communication of the blind bore 31, the transverse bore 30 and the further transverse bore 6.

Figure 3:
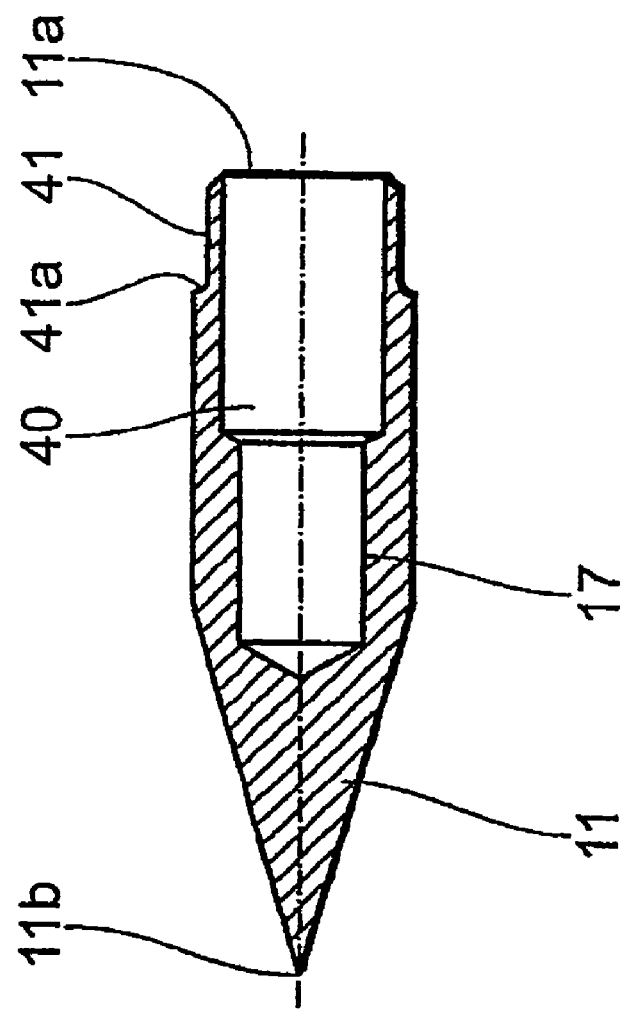
Figure 3:
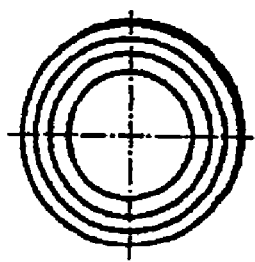

FIG. 3 shows a rear view and a sectional view of the probe tip 11. The probe tip 11 has a conical tip at its one distal end 11b. The probe tip 11 is cylindrical at its proximal end 11a. The proximal end 11a of the probe tip 11 has a stepped longitudinal bore 50 with a M1.4 screwthreaded bore 17. At its proximal end 11a the probe tip 11 further has a portion 41 of smaller outside diameter, thus producing a step 41a. The tip electrode 11 is preferably made from V2A steel.

Figure 4:
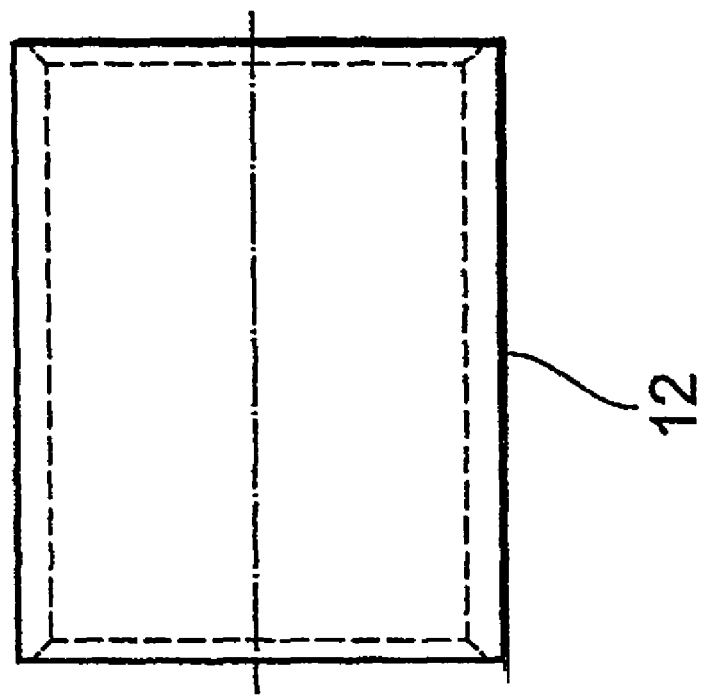
FIG. 4 shows a front view and a sectional view of an insulator ring 12 from FIG. 1b.
Figure 4:
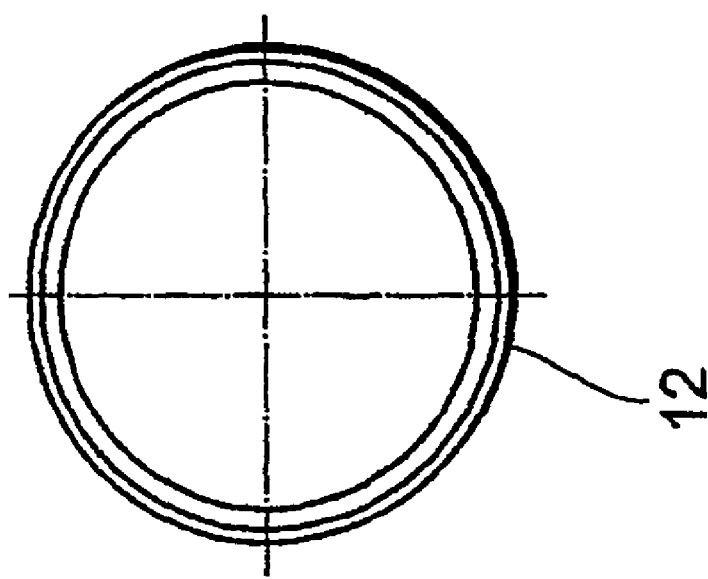

FIG. 4 shows a front view and a sectional view of the insulator ring 12. The inside diameter of the insulator ring 12 corresponds to the outside diameter of the portion 41 of the probe tip 11 so that the insulator ring 12 can be pushed onto the portion 41 of the probe tip 11. The insulator 12 is preferably made from PEEK (polyether ether ketone).

Figure 5:
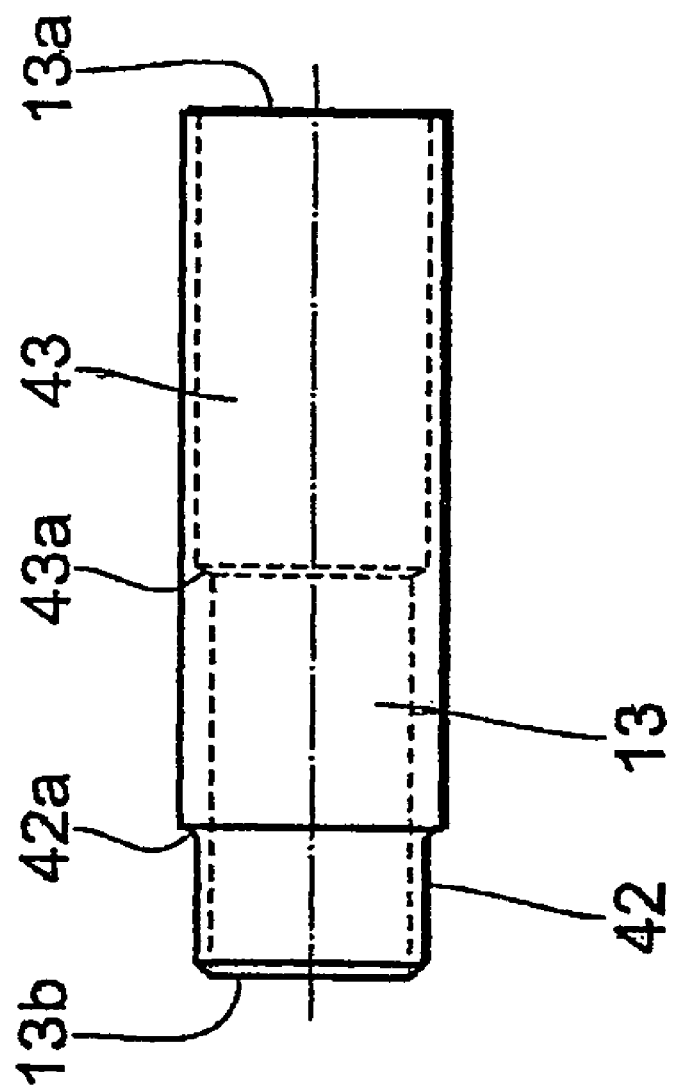
FIG. 5 shows a rear and a sectional view of a shaft electrode 13 from FIG. 1b.
Figure 5:
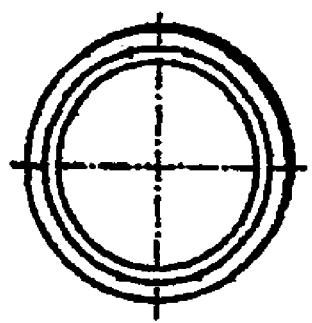

FIG. 5 shows a rear view and a sectional view of the shaft electrode 13. The shaft electrode 13 is of a substantially hollow-cylindrical configuration. At its distal end 13b the shaft electrode 13 has a portion 42 of smaller outside diameter, thus defining a step 42a. At the proximal end 13a of the shaft electrode 13 it has portion 43 of larger diameter, thus providing a further step 43a. The outside diameter of the portion 42 corresponds to the inside diameter of the insulator ring 12 so that the portion 42 can be introduced into the insulator ring 12. The inside diameter of the portion 43 further corresponds to the outside diameter of the outer conductor 19 so that the outer conductor 19 can be inserted into the shaft electrode 13 as far as the step 43a, in order in that way electrically to contact the electrode. In this case the shaft electrode 13 is preferably made from V2A steel.

In this arrangement the width of the insulator ring 12 is so selected that, when the insulator ring 12 is pushed onto the proximal end 11a of the probe tip 11 and the distal end 13b of the shaft electrode 13 is introduced into the insulator ring 12, there is a predetermined spacing between the tip electrode 11 and the shaft electrode 13.

Figure 6:
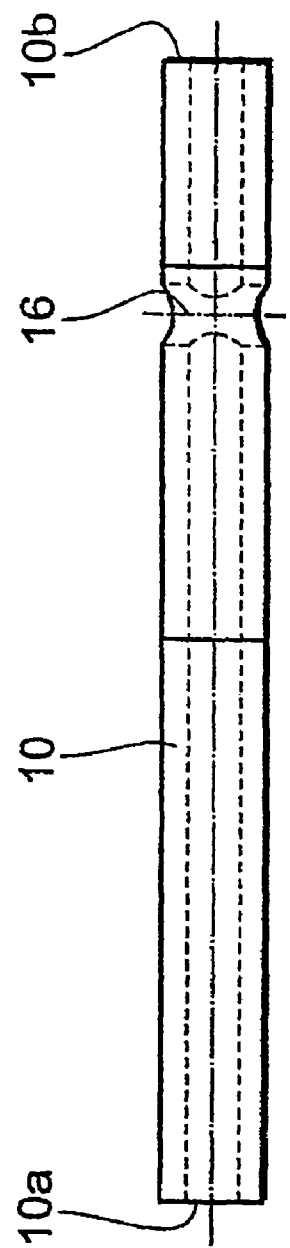
FIG. 6 shows a front and a sectional view of an inner conductor 10 from FIG. 1b.
Figure 6:
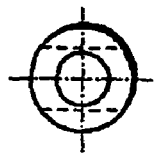

FIG. 6 shows a front view and a sectional view of the inner conductor 10. The inner conductor 10 has a M1.4 screwthread both at its proximal end 10a and also at its distal end 10b. At the distal end 10b the inner conductor 10 has a through bore 16 in transverse relationship with longitudinal axis. The M screwthread at the distal end 10b of the inner conductor 10 can be screwed into the screwthreaded bore 17 of the tip electrode 11 while the M screwthread at the proximal end 10a, when the probe is completely assembled, appears out of the longitudinal bore of the hand portion element 3. The inner conductor 10 can be screwed against the hand portion element 3 by means of the nut 80 which is screwed onto the M screwthread. This is depicted in FIG. 1c. The inner conductor 10 is preferably produced in the form of a metal tube from V2A steel. The use of a metal tube affords the advantage that the metal tube serves as an electrical feed line to the first electrode, for the supply of the cooling medium and for increasing stiffness and breaking strength.

Figure 7:
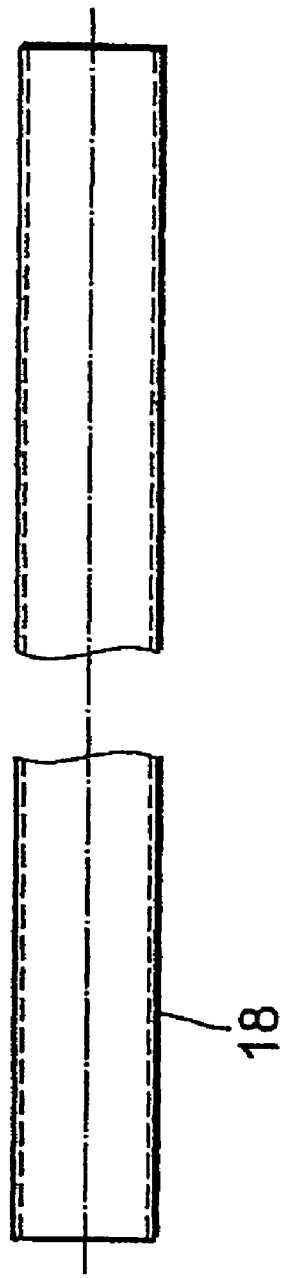
FIG. 7 shows a front and a sectional view of an insulator 18 from FIG. 1b.
Figure 7:
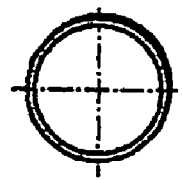

FIG. 7 shows a front view and a sectional view of the insulator 18 for the inner conductor 10. The insulator 18 is of a hollow-cylindrical configuration. In this case its inside diameter corresponds to the outside diameter of the inner conductor 10 so that the inner conductor 10 can be introduced into the insulator 18. In this case, the insulator 18—in the installed condition—extends from the proximal end of the blind bore 30 in the hand portion element 3 to shortly before the distal end of the shaft electrode 13 at the distal end of the probe. The insulation 18 is preferably made from PEEK plastic material.

Figure 8:
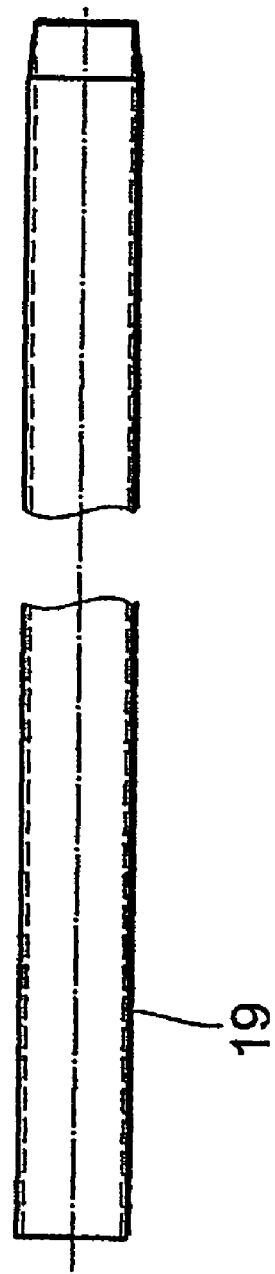
FIG. 8 shows a front and a sectional view of an outer conductor 19 from FIG. 1b.
Figure 8:
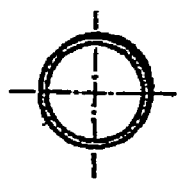

FIG. 8 shows a front view and a sectional view of the outer conductor 19. The outer conductor 19 is of a hollow-cylindrical configuration. The outside diameter of the outer conductor 19 corresponds to the inside diameter of the portion 43 of the shaft electrode 13 so that the distal end 19b of the outer conductor 19 can be introduced into the proximal end 13a of the shaft electrode 13 as far as the step 43a. The outer conductor 19 further extends through the blind bore 9 to the level of the clamping ring 5 in the hand portion element 3. In the blind bore 9, the outer conductor 9 is contacted by an electrically conductive spring wire 8. The outer conductor 19 is preferably made from V2A steel.

Figure 9:
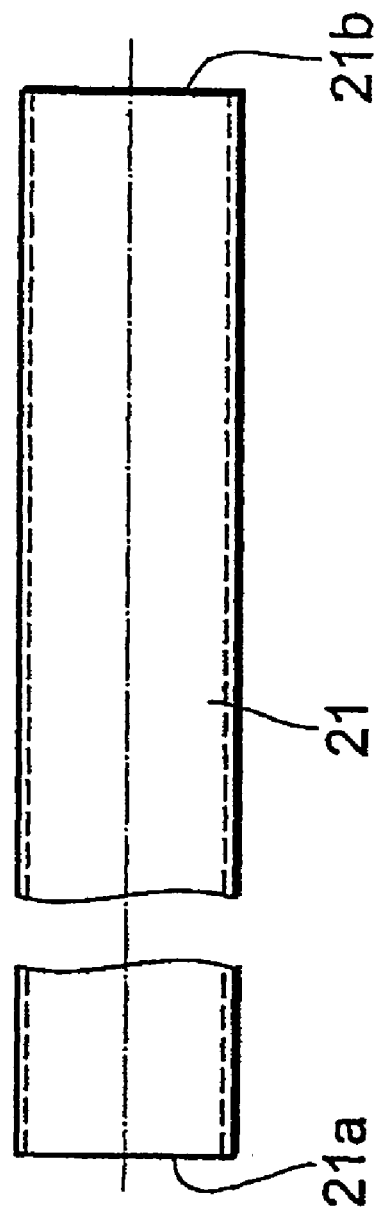
FIG. 9 shows a front and a sectional view of an insulation tube 21 from FIG. 1b.
Figure 9:
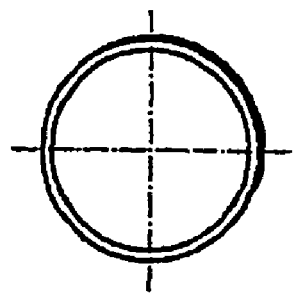

FIG. 9 shows a front view and a sectional view of the insulation tube 21. In this case the insulation tube 21 serves for insulation of the outer conductor 19 in relation to adjoining tissue and is of a hollow-cylindrical configuration. The inside diameter of the insulation tube 21 corresponds to the outside diameter of the outer conductor 19 so that the outside insulation 21 can be passed over the outer conductor 19. The outside insulation 21 adjoins the proximal end 13a of the shaft electrode 13 and extends in the proximal end direction to the level of the clamping ring 5 in the hand portion element 3. In this case the insulation tube 21 is preferably made from FEP (Teflon®), PPSU (Polyphenylsulfone), PE (Polyethylene) or PEEK plastic material.

Figure 10:
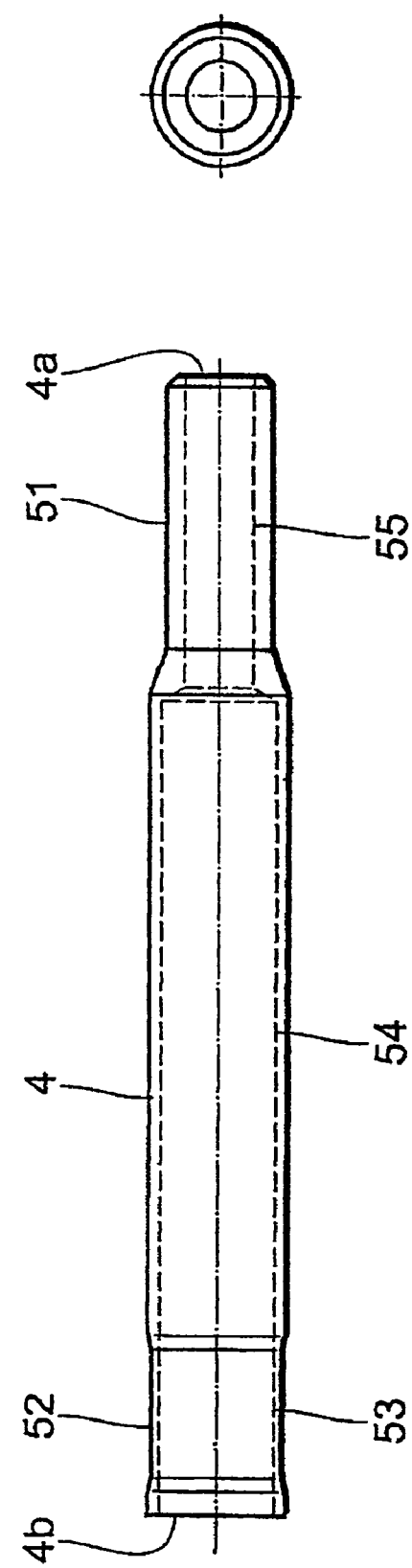
FIG. 10 shows a rear and a sectional view of a second hand portion element 4 from FIG. 1a, FIG. 11 shows a front and a sectional view of a clamping ring 5 from FIG. 1a, FIG. 12 shows a front and a sectional view of a first hand portion element 3 from FIG. 1a, and FIG. 13 shows a sectional view of a probe arrangement according to the state of the art.

FIG. 10 shows a rear view and a sectional view of the hand portion element 4. The hand portion element 4 has a proximal end 4a and a distal end 4b and is of a substantially hollow-cylindrical configuration. However it has a first portion 51 of smaller outside diameter and a second portion 52 also of smaller outside diameter. The element 4 has a stepped longitudinal bore, the inside diameter of the portion 53 of the longitudinal bore at the distal end 4b being larger than the inside diameter of the portion 55 at the proximal end 4a. The portion 53 is of a fluted configuration. The hand portion element 4 is preferably made from POM (Polyoxymethylene) plastic material.

Figure 11:
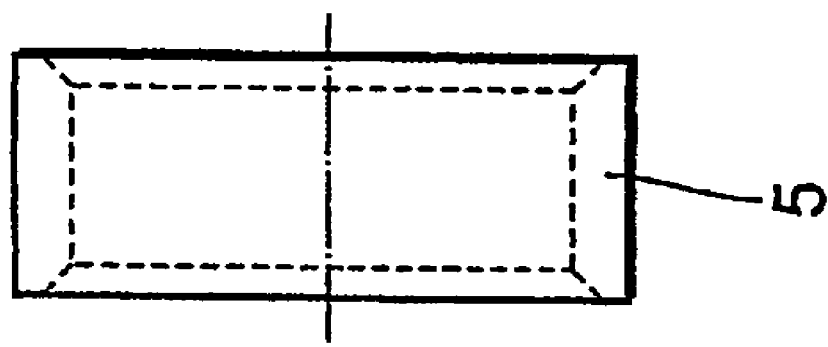
Figure 11:
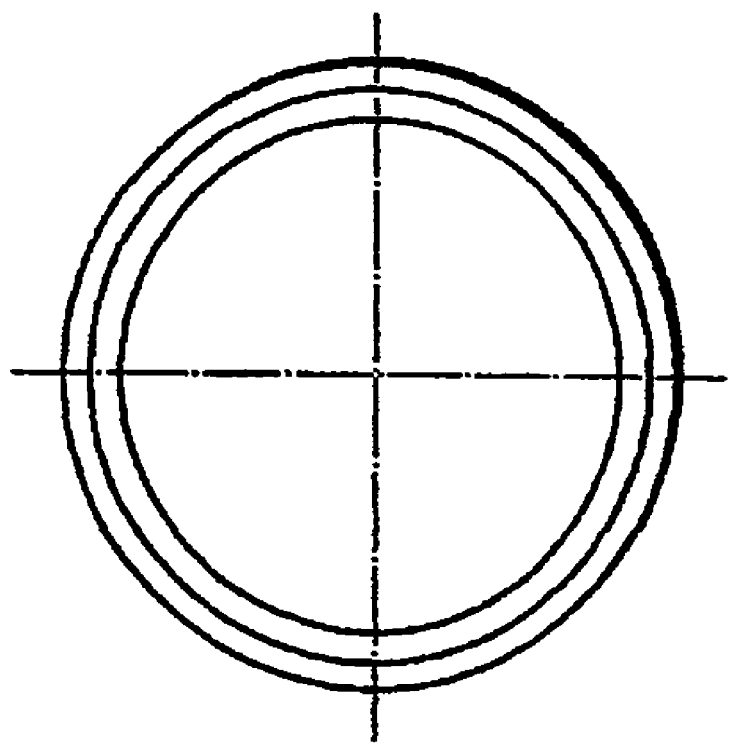

FIG. 11 shows a front view and a sectional view of the clamping ring 5. The outside diameter of the clamping ring 5 corresponds to the inside diameter of the portion 53 of the hand portion element 4, so that the clamping ring 5 can be introduced into the distal end 4b of the hand portion element 4. The clamping ring 5 is preferably made from POM plastic material.

Figure 12:
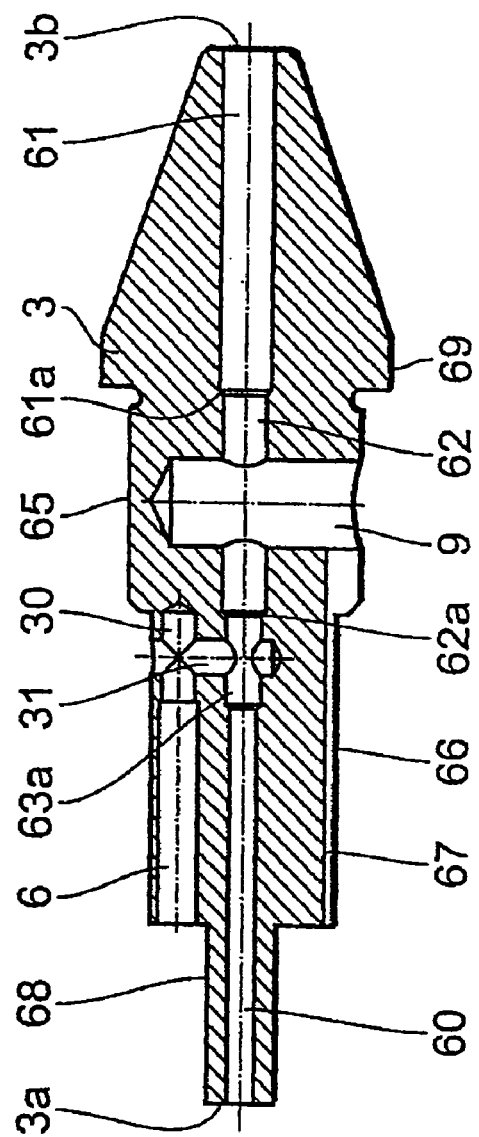
Figure 12:
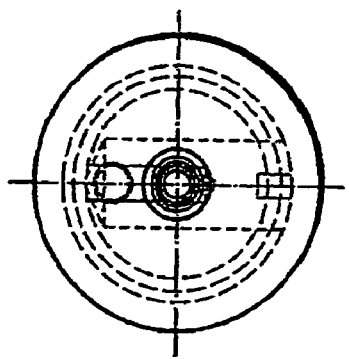
Figure 13:
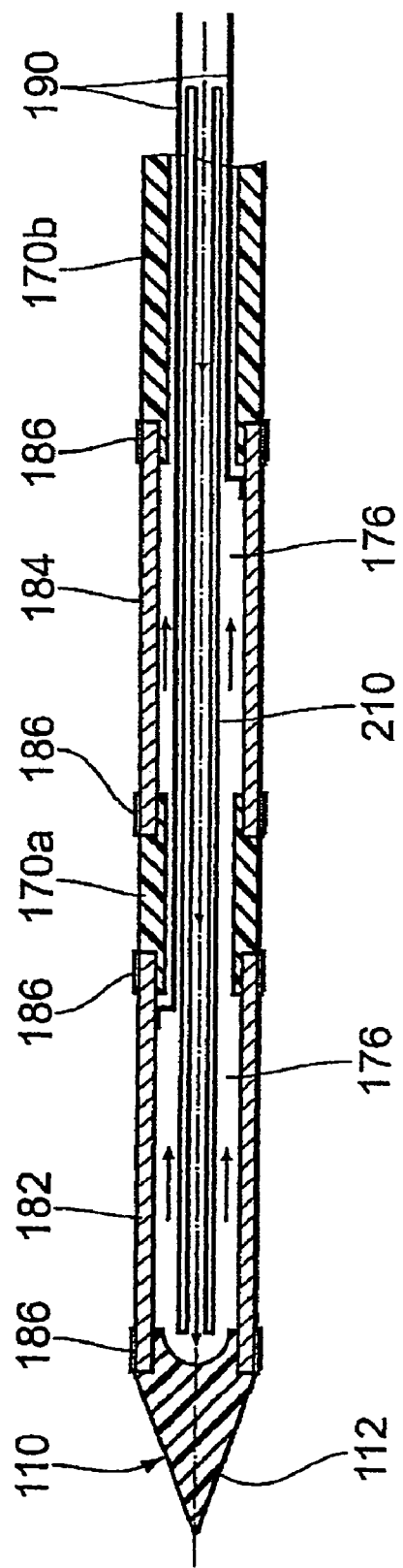

FIG. 12 shows a front view and a sectional view of the hand portion element 3 having a distal end 3b and a proximal end 3a. The hand portion element 3 is of a substantially cylindrical nature, wherein the distal end 3b is of a frustoconical configuration. The hand portion element 3 has a stepped longitudinal bore 60. Towards the proximal end 3a the element 3 has three different portions 69, 65, 66 and 68 each of progressively smaller outside diameters. In this case the portion 65 is of a fluted configuration and has a blind bore 9. The portion 66 has a further blind bore 31 as well as transverse bores 6 and 30, wherein the blind bore 31 crosses the transverse bore 30 and the transverse bore 6 goes into the transverse bore 30. The stepped longitudinal bore 60 can be divided into different portions 61, 62 and 63, wherein the inside diameter of those portions decreases from the distal end 3b of the hand portion element 3 to the proximal end 3a of the hand portion element 3. In this case the inside diameter of the portion 61 corresponds to the outside diameter of the outside insulation 21, the inside diameter of the portion 62 corresponds to the outside diameter of the outer conductor 19, the inside diameter of the portion 63 corresponds to the outside diameter of the insulator 18 and the inside diameter of the portion 60 corresponds to the outside diameter of the inner conductor 10. Accordingly the proximal end of the insulator 18 extends as far as the step 63a, that of the outer conductor 19 as far as the step 62a and that of the outside insulation 21 as far as the step 61a. In contrast the inner conductor 10—in the inserted condition—projects from the proximal end 3a of the hand portion element 3.

The hand portion element 3 further has a slot 67 which extends from the proximal end 3a along the portions 66 and 65 to the blind bore 9. That slot 67 serves to receive the electrically conductive spring wire 8 for electrical contacting of the outer conductor 19 in the blind bore 9. The outside diameter of the portion 66 corresponds to the inside diameter of the clamping ring 5 so that the clamping ring 5 can be pushed onto the portion 66. The outside diameter of the portion 65 corresponds to the inside diameter of the portion 53 of the hand portion element 4 so that the hand portion element 3 can be introduced into the hand portion element 4. The hand portion element 3 is preferably made from POM plastic material.

The opening of the blind bore 31 is closed by pushing the clamping ring 5 onto the portion 66 of the hand portion element 3. In addition, the opening of the blind bore 6 is closed by inserting the hand portion element 3 into the hand portion element 4.

A tube or the like can be introduced into the bore 6 and a tube or hose can be connected to that tube, wherein the fluid flowing back from the distal end by way of the intermediate space 20 can be discharged through the tube or hose. In addition a tube or hose can be connected to the proximal end 10a of the inner conductor 10 so that fluid can be pumped from the proximal end of the probe into the distal end of the probe by way of the hollow duct 15 of the inner conductor 10.

The invention claimed is:

1. A probe arrangement for the electrothermal coagulation of tissue comprising a distal probe tip and a proximal hand portion, comprising
    at least a first and a second electrode in the region of the distal probe tip, said electrodes being disposed on the exterior of the probe;
    an inner conductor having a distal end and a proximal end, wherein the inner conductor extends from the distal probe tip to the proximal hand portion and is adapted to electrically contact the first electrode in the distal probe tip;
    an outer conductor which extends from the distal probe tip to the proximal hand portion and is adapted to electrically contact the second electrode in the distal probe tip;
    an insulator arranged between the inner and outer conductors and adapted to electrically insulate the inner conductor from the outer conductor; and
    means for bracing the inner conductor in relation to the outer conductor in such a way that the inner conductor is under tensile stress and the outer conductor is under compression stress, said bracing means including a threaded portion on said inner conductor and a nut engaging said threaded portion and bracing against a portion of said hand portion;
    characterized in that flexural stiffness of the probe arrangement is provided due to the inner conductor being under tensile stress between the probe tip and the hand portion and further characterized in that the inner conductor has a hollow duct which is adapted to pass cooling or heating fluid from the proximal end to the distal end of the inner conductor, and a through bore which is adapted to allow the heating or cooling fluid supplied through the hollow duct to be discharged from the hollow duct, and provided between the insulator and the outer conductor is an intermediate space which is adapted to pass the cooling or heating fluid of the hollow duct, which is flowing out of the through bore, back to the proximal end.

2. A probe arrangement as set forth in claim 1 further comprising a force-locking and/or positively-locking connection that connects the inner conductor to the hand portion and also to the probe tip.

3. A probe arrangement as set forth in claim 2 characterized in that the inner conductor is connected by a screw connection both to the hand portion and also to the probe tip.

4. A probe arrangement as set forth in claim 1 characterized in that the inner conductor is in the form of a metal tube.

5. A probe arrangement as set forth in claim 4 characterized in that the inner and outer conductors and the insulator are arranged coaxially relative to each other.

6. A probe arrangement as set forth in claim 1 characterized in that the distal end of the inner conductor is screwed to the probe tip and the proximal end of the inner conductor is braced in relation to the hand portion.

7. A probe arrangement as set forth in claim 1 characterized in that the first electrode is in the form of a tip electrode.

8. A probe arrangement as set forth in claim 1 characterized in that the second electrode is in the form of a shaft electrode.

9. A probe arrangement as set forth in claim 1 characterized in that the first electrode is in the form of a tip electrode, the second electrode is in the form of a shaft electrode and arranged between the tip electrode and the shaft electrode is an insulator element which is adapted to insulate the tip electrode from the shaft electrode.

10. A probe arrangement as set forth in claim 9 characterized in that the insulator element is of an annular configuration.

11. A probe arrangement as set forth in claim 1 characterized by an insulation tube which insulates the outer conductor outwardly.

12. A probe arrangement as set forth in claim 11 wherein the hand portion has a first hand portion element which is adapted to receive the proximal ends of the inner conductor, the outer conductor, the insulator and the insulation tube.

13. A probe arrangement as set forth in claim 12 characterized in that the first hand portion element has a first blind bore and a longitudinal slot between the proximal end of the first hand portion element and the first blind bore, which is adapted to pass an electrically conductive spring wire from the proximal end of the first hand portion element to the outer conductor in the first blind bore in order to electrically contact the outer conductor.

14. A probe arrangement as set forth in claim 11 characterized in that the first hand portion element has a transverse bore and a second blind bore which cross each other and are adapted to provide a communication between the proximal end of the hand portion element and the intermediate space.

15. A probe arrangement as set forth in one of claims 4, 6, 5, and 7-12 characterized in that at its proximal end the inner conductor has a male screwthread which is adapted to brace the inner conductor with a screwthreaded nut in relation to the first hand portion element.

16. A probe arrangement as set forth in claim 1 characterized by an electrically little-conducting or non-conducting cooling fluid, preferably deionized water, wherein said fluid is circulated toward the distal end of said probe through said hollow duct and then away from said distal end via said intermediate space.

* * * * *